(12) United States Patent
Douglass

(10) Patent No.: US 9,208,284 B1
(45) Date of Patent: Dec. 8, 2015

(54) MEDICAL PROFESSIONAL APPLICATION INTEGRATION INTO ELECTRONIC HEALTH RECORD SYSTEM

(71) Applicant: Practice Fusion, Inc., San Francisco, CA (US)

(72) Inventor: Matthew Christopher Douglass, San Francisco, CA (US)

(73) Assignee: Practice Fusion, Inc., San Francisco, CA (US)

( * ) Notice: Subject to any disclaimer, the term of this patent is extended or adjusted under 35 U.S.C. 154(b) by 0 days.

(21) Appl. No.: 14/318,492

(22) Filed: Jun. 27, 2014

(51) Int. Cl.
*G06F 7/04* (2006.01)
*G06F 17/30* (2006.01)
*G06F 19/00* (2011.01)
*H04L 29/06* (2006.01)

(52) U.S. Cl.
CPC .............. *G06F 19/322* (2013.01); *H04L 63/08* (2013.01)

(58) Field of Classification Search
None
See application file for complete search history.

(56) References Cited

U.S. PATENT DOCUMENTS

| | | | |
|---|---|---|---|
| 2003/0028664 A1* | 2/2003 | Tan et al. | 709/237 |
| 2008/0244722 A1* | 10/2008 | Satish et al. | 726/9 |
| 2013/0110547 A1* | 5/2013 | Englund et al. | 705/3 |
| 2014/0109197 A1* | 4/2014 | Schneider et al. | 726/4 |

* cited by examiner

*Primary Examiner* — Valerie Lubin
(74) *Attorney, Agent, or Firm* — Sterne, Kessler, Goldstein & Fox P.L.L.C.

(57) ABSTRACT

Embodiments relate to integrating data collection and productivity applications with an EHR system. To integrate a patient's data collection application with the EHR system, an EHR server provides API calls to (i) retrieve patient information, (ii) post data to the patient's account, and (iii) post data to the medical professional's account. To integrate a medical professional's productivity application with the EHR system, an EHR server provides API calls to (i) retrieve practice information, (ii) retrieve patient information, and (iii) post data to the medical professional's account. Embodiments securely provide these APIs to third party providers.

21 Claims, 14 Drawing Sheets

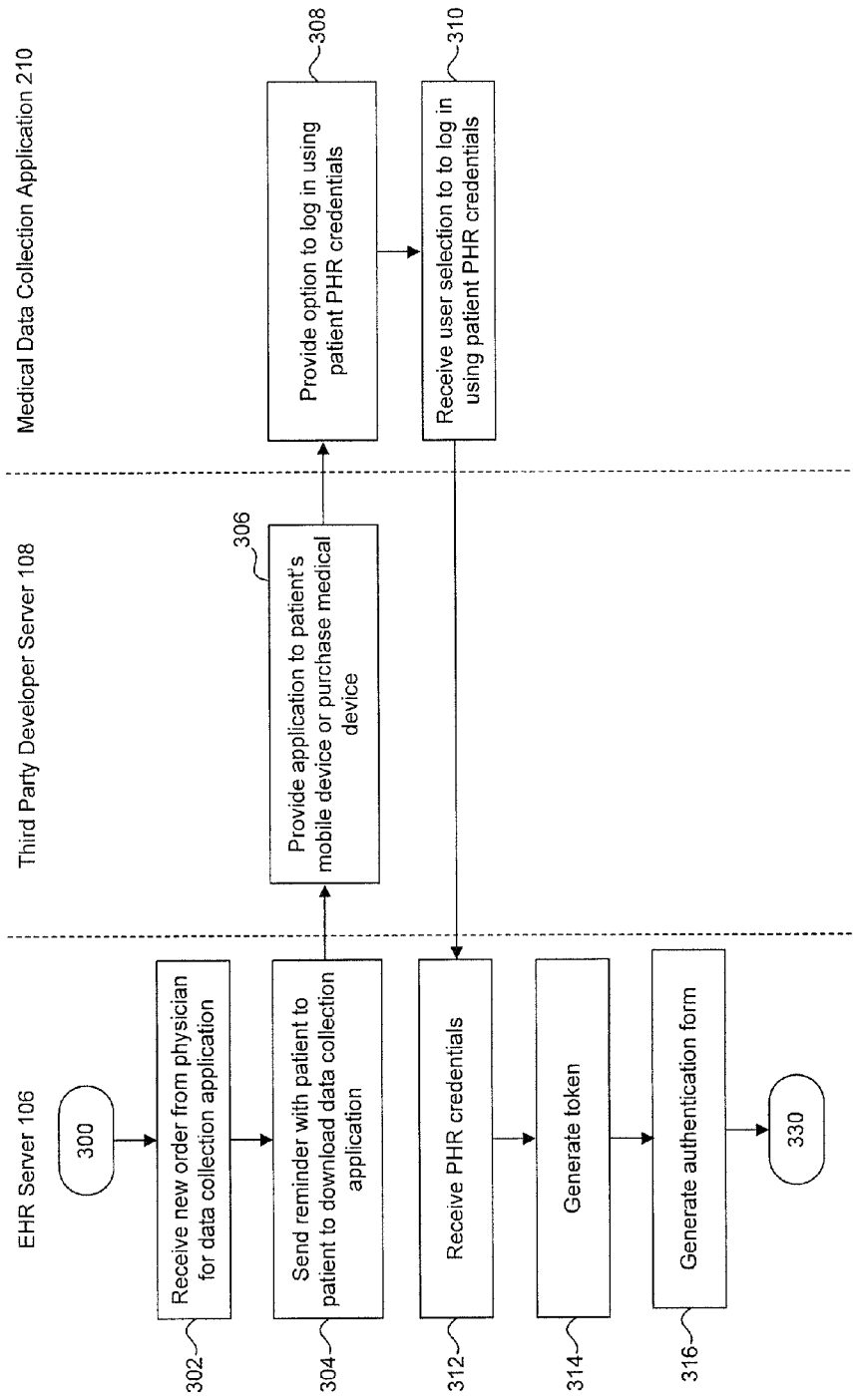

FIG. 7

MEDICAL PROFESSIONAL APPLICATION INTEGRATION INTO ELECTRONIC HEALTH RECORD SYSTEM

BACKGROUND

1. Field

This field is generally related to presenting electronic health records.

2. Background

Electronic Health Records

Medical records related to a patient's health information are essential to the practice of medical care. Traditionally, medical records were paper-based documents. The emergence of electronic health record (EHR) systems offers medical professionals and patients with new functionalities that paper-based medical records cannot provide. An EHR, sometimes known as electronic medical record (EMR), is a collection of electronically stored information about an individual patient's lifetime health status and health care. EHRs may include a broad range of data, including demographics, medical history, medication and allergies, immunization status, laboratory test results, radiology images, vital signs, personal statistics like age and weight, and billing information. Many commercial EHR systems combine data from a number of health care services and providers, such as clinical care facilities, laboratories, radiology providers, and pharmacies.

EHRs are a drastic improvement over paper-based medical records. Paper-based medical records require a large amount of storage space. Paper records are often stored in different locations, and different medical professionals may each have different and incomplete records about the same patient. Obtaining paper records from multiple locations for review by a health care provider can be time consuming and complicated. In contrast, EHR data is stored in digital format, and thus can be accessed from anywhere. EHR systems significantly simplify the reviewing process for health care providers. Because data in EHRs can be linked together, EHRs vastly improve the accessibility of health records and the coordination of medical care.

EHRs also decrease the risk of misreading errors by health care professionals. Poor legibility is often associated with handwritten, paper medical records, which can lead to medical errors. EHRs, on the other hand, are inherently legible given that they are typically stored in typeface. In addition, electronic medical records enhance the standardization of forms, terminology and abbreviations, and data input, which help ensure reliability of medical records. Further, EHRs can be transferred electronically, thus reducing delays and errors in recording prescriptions or communicating laboratory test results.

The benefits of digitizing health records are substantial. Health care providers with EHR systems have reported better outcomes, fewer complications, lower costs, and fewer malpractice claim payments. But despite EHRs' potential in drastically improving the quality of medical care, only a low percentage of health care providers use EHR systems. While the advantages of EHRs are significant, they also carry concerns, including security and privacy risks, high costs, lost productivity during EHR implementation or computer downtime, and lack of EHR usability.

The Health Insurance Portability and Accountability Act (HIPAA), enacted in the U.S. in 1996, establishes rules for access, authentication, storage, auditing, and transmittal of medical records. HIPPA sets a limit as to what health information can be disclosed to third parties, and who can view a patient's medical records. HIPPA protects information in electronic medical records, such as information doctors and nurses input, recorded conversations between a doctor and a patient, and billing information. The HIPAA Security Rule, effective on Apr. 20, 2005 for most covered entities, adds additional constraints to electronic data security and the storage and transmission of private health information (PHI). Despite the regulatory restrictions, privacy and security threats are still a major risk of the current EHR systems. The convenient and fast access to patients' health records through an EHR system introduces a host of security concerns. Medical information in digital format is vulnerable to various privacy exploitations associated with hacking, computer theft, malicious attack, or accidental disclosure. According to some estimates, between 250,000 and 500,000 patients experience medical identity theft every year.

Additionally, the high cost of EHRs also significantly hinders EHR adoption. A large number of physicians without EHRs have referred to initial capital costs as a barrier to adopting EHR systems. Cost concerns are even more severe in smaller health care settings, because current EHR systems are more likely to provide cost savings for large integrated institutions than for small physician offices. During EHR technology's implementation, productivity loss can further offset efficiency gains. The need to increase the size of information technology staff to maintain the system adds even more costs to EHR usages.

Usability is another major factor that holds back adoption of EHRs. It is particularly challenging to develop user-friendly EHR systems. There is a wide range of data that needs to be integrated and connected. Complex information and analysis needs vary from setting to setting, among health care provider groups, and from function to function within a health care provider group. To some providers, using electronic medical records can be tedious and time consuming, and the complexity of some EHR systems renders the EHR usage less helpful. Some doctors and nurses also complain about the difficulty and the length of time to enter patients' health information into the system.

Under-utilization of EHR systems, despite incentives and mandates from the government and the tremendous potential of EHRs in revolutionizing the health care system, calls for better EHR systems that are secure, cost-effective, efficient, and user-friendly.

Comprehensive EHR systems can provide capabilities far beyond simply storing patients' medical records. Because EHR systems offer health care providers and their workforce members the ability to securely store and utilize structured health information, EHR systems can have a profound impact on the quality of the health care system. In Framework for Strategic Action on Health Information Technology, published on Jul. 21, 2004, the Department of Health & Human Services (HHS) outlined many purposes for EHR services. The outlined purposes include, among other things, improving health care outcomes and reducing costs, reducing record-keeping and duplication burdens, improving resource utilization, care coordination, active quality and health status monitoring, reducing treatment variability, and promoting patients' engagement in and ownership over their own health care.

Recent legislation has set goals and committed significant resources for health information technology (IT). One of the many initiatives of the American Recovery and Reinvestment Act of 2009 (ARRA) was "to increase economic efficiency by spurring technological advances in science and health." The Health Information Technology for Economic and Clinical Health (HITECH) Act, passed as a part of ARRA, allocated billions of dollars to adopt meaningful use of EHRs in the health care system. HITECH also mandates the Office of the National Coordinator for Health Information Technology (ONC) to define certification criteria for "Certified EHR Technology."

EHR systems satisfying "Certified EHR Technology" criteria are capable of performing a wide range of functions, including: entry and storage, transmission and receipt of care summaries, clinical decision support, patient lists and education resources, generation of public health submission data, and patient engagement tools. Entry and storage is related to the ability to enter, access and modify patient demographic information, vital signs, smoking status, medications, clinical and radiology laboratory orders and results. Transmission and receipt of care summaries involve the ability to receive, incorporate, display and transmit transition of care/referral summaries. Clinical decision support features configurable clinical decision support tools, including evidence-based support interventions, linked referential clinical decision support, and drug-drug and drug-allergy interaction checks. Patient lists and education resources include the ability to create patient lists based on problems, medications, medication allergies, demographics and laboratory test result values, and the ability to identify patient-specific education resources based on such data elements. Generating public health submission data allows users to create electronic immunization and syndromic surveillance data files that can be submitted to public health agencies. Patient engagement tools allow medical professionals to grant patients with an online means to view, download and transmit their health information to a third party, provide patients with clinical summaries after office visits, and facilitate secure-doctor patient messaging.

Patient and Physician Devices

Devices exist that observe aspects of a patient's health. For example, a blood glucose monitor available from Agamatrix Inc. of Salem, N.H. collects blood glucose readings using a smartphone application. In addition, devices exist that improve a doctor's productivity. For example, healthcare speech recognition solutions available from Nuance Inc. of Salem, N.H. enable a doctor to dictate healthcare information.

These devices do not directly integrate with current EHR systems. For the data produced by these systems to be entered into an EHR, it often must be manually retyped into the patient record within the EHR. Or, in some cases the collected data may be sent to a doctor's practice as a fax, which must be converted to a PDF and imported into the patient's record.

BRIEF SUMMARY

In an embodiment, a computer-implemented method integrates a practice productivity application into an electronic health records (EHR) system. In the method, an API call to retrieve patient or practice data from a medical records database on the EHR system is received. The API call includes a persistent security token for the medical professional and a persistent security token for a developer of the practice productivity application. In response to receipt of the API call, authenticity of the persistent security token for the medical professional and the persistent security token for the practice productivity application is verified. And whether the medical professional has authorized the practice productivity application to retrieve the medical professional's patient or practice data from the medical records database is determined. If the medical professional's and developer's security tokens are determined to be authentic and the medical professional is determined to have authorized the practice productivity application to retrieve the medical professional's patient or practice data, the patient or practice data is sent to the practice productivity application such that the practice productivity application provides a user experience customized according to the patient or practice data.

Method and computer program product embodiments are also disclosed.

Further embodiments, features, and advantages of the invention, as well as the structure and operation of the various embodiments, are described in detail below with reference to accompanying drawings.

BRIEF DESCRIPTION OF THE DRAWINGS

The accompanying drawings, which are incorporated herein and form part of the specification, illustrate the present disclosure and, together with the description, further serve to explain the principles of the disclosure and to enable a person skilled in the relevant art to make and use the disclosure.

FIGS. 3A-D are flowcharts illustrating example methods to integrate the patient data collection device and the EHR server.

FIG. 7 is an illustration of a conventional medical record.

The drawing in which an element first appears is typically indicated by the leftmost digit or digits in the corresponding reference number. In the drawings, like reference numbers may indicate identical or functionally similar elements.

DETAILED DESCRIPTION

Embodiments relate to integrating data collection and practice productivity applications with an EHR system. In the detailed description that follows, references to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

Integration APIs

Figure 1:
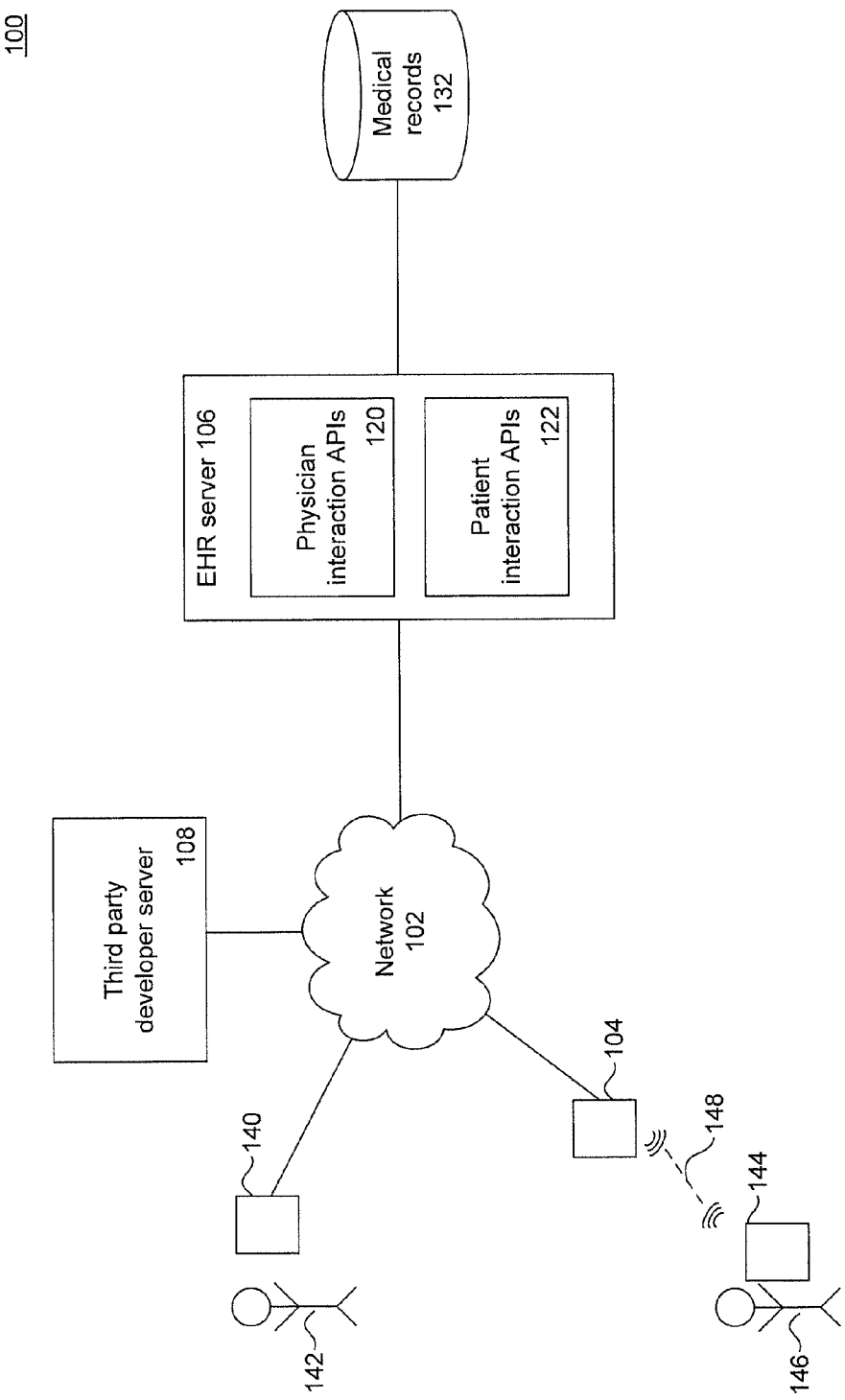
FIG. 1 is a diagram illustrating a system that integrates a patient data collection device and a physician productivity device with an EHR server.

FIG. 1 is a diagram illustrating a system 100 that integrates a patient data collection device and a physician productivity device with an EHR server. System 100 includes an EHR server 106 that communicates over one or more networks 102, such as the Internet, with a third-party developer server 108, a mobile device 140, and a mobile device 104.

EHR server 106 interacts with a medical records database 132. Medical records database 132 stores a history describing the health and treatment of various patients. Some of the stored data may be only accessible to the patient. Other data stored in medical records database 132 may be accessible to both the physician and patient. Still other data may be accessible only to the physician. Medical record database 132 may, for example, store records of observational data, patient encounters, lab results, prescriptions, and messages. In addition, medical records database 132 can include biographical information about a patient, such as name, address, date of birth, and information about a physician's practice, such as specialty and number of employees.

Third-party developers may develop applications that would benefit from interacting with medical records database 132. In an example, a third-party developer may want its application to be able to download patient biographical information, patient records, or practice information and automatically customize operation, without having the patient or physician manually reenter the information. In another example, an application may submit additional data to medical records database 132 to the patient's records, to the physician's records, or to both. To enable these applications to interact with medical records database 132, EHR server 106 offers two sets of APIs: physician interaction APIs 120 and patient interaction APIs 122. Physician interaction APIs 120 may be designed to interact with applications that increase physician productivity, and patient interaction APIs 122 may be designed to interact with applications that collect observational data about a patient.

The various applications may communicate with EHR server 106 via a network 102. The applications may include a mobile device, and that mobile device may communicate directly with EHR server 106. Or the mobile device may communicate with third-party developer server 108, and third-party developer server 108 may communicate with EHR server 106.

Diagram 100 shows two mobile devices: mobile device 104 and mobile device 140. Mobile device 104 has a user 146, and mobile device 140 has a user 142. As mentioned above, users 142 and 146 may be patients or physicians. They could also be caretakers or other medical professionals such as office staff or nurses. Users 142 and 146 may download client applications that run on mobile device 140 and mobile device 142, and interact with EHR server 106.

As mentioned above, the client applications on mobile devices 104 and 140 may communicate over network 102 to submit data to EHR server 106. Network 102 may be, for example, a wide area network, such as the Internet. In some embodiments, the client applications may also interact with devices local to the user. In diagram 100, this is shown with a device 144.

Device 144 may be a data collection device that communicates with mobile device 104 using a short-range communication channel 148. Short-range communication channel 148 may, for example, be a wired connection, such as through a USB port or audio jack of mobile device 104. In addition or alternatively, short-range communication channel 148 may be a wireless connection, such as a Bluetooth or Wi-Fi connection. In an example, device 144 may be activity vital signs tracker, such as an AGAMATRIX blood glucose monitor, made by Agamatrix, Inc. of Salem, N. Mex., that blood glucose levels. In other examples, device 144 may be an activity tracker. Device 144 may communicate observational data describing the movement to mobile device 104 via short-range communication channel 148. Mobile device 104 may submit that observational data to EHR server 106 using patient interaction APIs 122. Once received at EHR server 106, the observational data may be stored with the patient's health records in medical records database 132. In this way, embodiments can integrate a patient data collection device with an EHR server.

In addition or alternatively to integrating patient data collection devices with an EHR server, some embodiments integrate practice productivity applications with an EHR server. For example, a mobile device 140 may include a practice productivity application, such as a transcribing application. Patient productivity applications may benefit from knowing information about a particular patient, such as the patient that the physician is currently scheduled to see. To retrieve this information, a practice productivity application may send a request for patient information to EHR server 106 using physician interaction APIs 120. On receipt of the request, EHR server 106 may retrieve the patient information from medical records database 132 and return the patient information to mobile device 104 via network 102. In this way, embodiments can integrate a practice productivity application with an EHR server.

The detailed description that follows describes operation of the APIs in more detail. In particular, integration of the patient collection device and EHR server is described in more detail below with respect to FIG. 2 and FIGS. 3A-D. Integration of the practice productivity application and EHR server is described in more detail below with respect to FIG. 4 and FIGS. 5A-E.

Integration of Patient Data Collection Device and EHR Server

Figure 2:
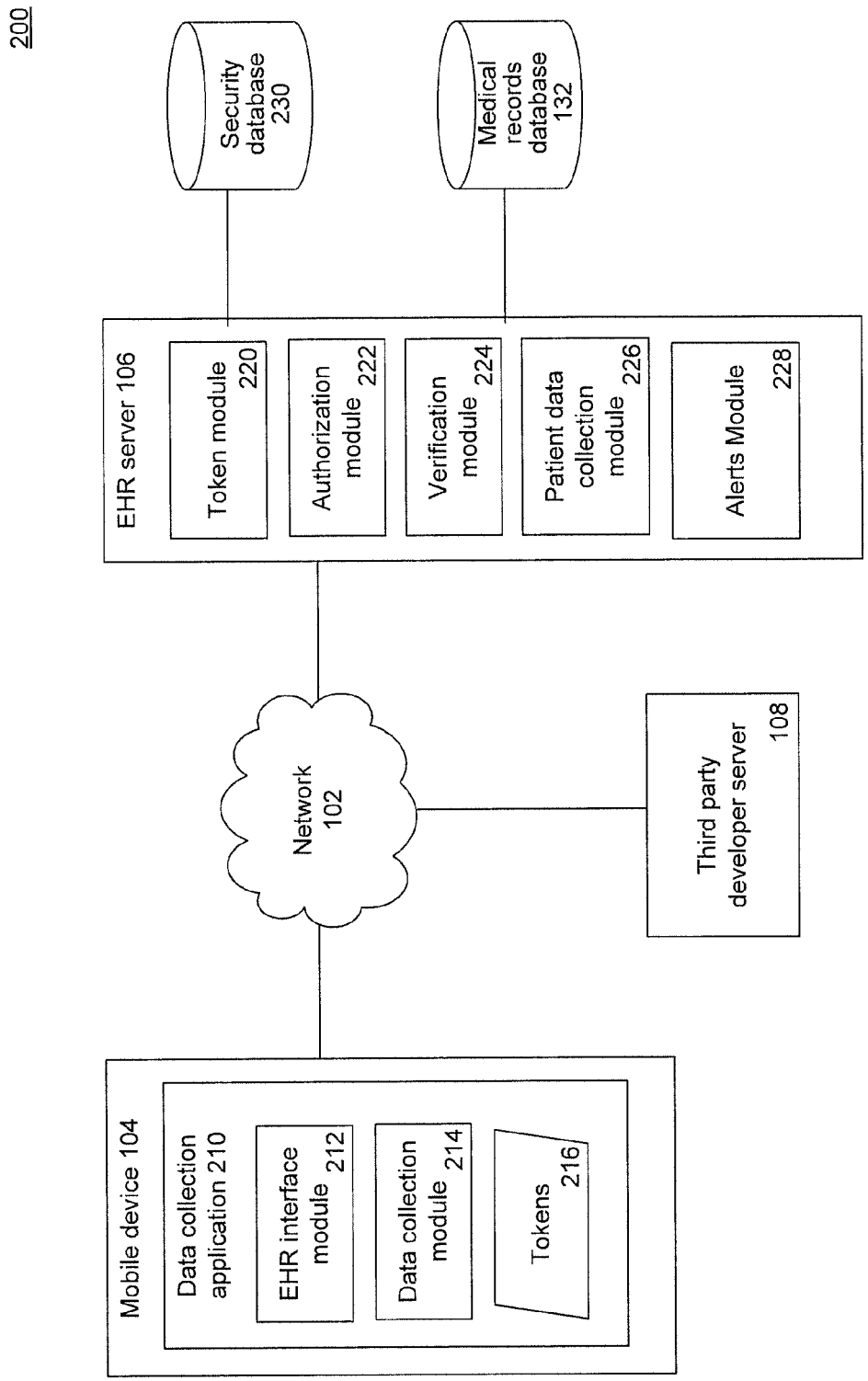
FIG. 2 is a diagram illustrating the patient data collection device and the EHR server of FIG. 1 in greater detail.

FIG. 2 is a diagram illustrating a system 200 that integrates a patient data collection device and an EHR server. Like system 100 in FIG. 1, system 200 includes mobile device 104, network 102, third-party developer server 108, EHR server 106, and medical records database 132. In addition to medical records database 132, EHR server 106 is coupled to a security database 230.

Mobile device 104 includes a data collection application 210 that collects observational data about the patient. For example, data collection application 210 may collect vital signs data or observation of daily living (ODL) data. Data collection application 210 may, for example, be prescribed by a physician. For example, a physician may prescribe a blood glucose monitor to manage diabetes. In other embodiments, data collection application 210 may be physician prescription or may be obtained without needing a physician's direction. Data collection application 210, may, for example, be purchased or retrieved from an online application marketplace.

Data collection application 210 includes an EHR interface module 212, a data collection module 214, and security tokens 216. EHR interface module 212 communicates with EHR server 106 via network 102. To communicate with EHR server 106, EHR interface module 212 may send messages formatted according to a particular application programming interface (API). The messages may be, for example, web service requests. They may include certain parameters specifying the action requested from EHR server 106 and may be formatted as specified by the API. In response, EHR interface module 212 will receive the requested data from EHR server 106. The data transmitted in response may also be formatted as specified by the API. In one example, the messages to and from EHR server 106 may be formatted as structured XML messages.

Data collection module 214 collects observation of daily living (ODL) data from a user. In one embodiment, a user may directly enter the data into an interface presented by data collection module 214. The interface may, for example, periodically prompt the user for the data. In another embodiment, mobile device 104 may be equipped with sensors that data collection module 214 uses to collect the data. For example, mobile device 104 may have accelerometer and GPS sensors that can be used to detect movement. In another example, mobile device 104 may have a camera that can be used to collect medical data, such as healing of a wound over time. In yet another embodiment, data collection module 214 may interact with other devices using mobile device 104's short-range communication channels. The other devices can be equipped with sensors to detect the ODL data. Examples of these types of devices include blood glucose monitors, activity trackers, and digital scales.

Finally, data collection application 210 includes tokens 216. Tokens 216 are persistent security tokens that can be used to identify and authenticate the data collection application 210 or its user. Tokens 216 may include a token for the developer. For example, the provider of EHR server 106 may require that any application that interacts with it is pre-certified. The developer may request access to EHR server 106's API from an EHR provider. After the provider has reviewed the application and determined that it is safe, secure, and medically appropriate, the provider may grant access to the applications provided by the developer. To grant access, the provider may issue a persistent security token that can be used to ensure that the API requests from data collection module 210 are valid and authorized.

To access medical records database 132, a mobile device 104 sends requests via network 102 to EHR server 106. As described above, the request may come directly from mobile device 104. Or, data collection application 210 may be in communication with third-party developer server 108, and third-party developer server 108 may send the API request to EHR server 106. To service the API requests, in an embodiment EHR server 106 includes five modules: token module 220, authorization module 222, verification module 224, patient data collection module 226, and alert module 228. Each module is discussed below.

Token module 220, authorization module 222, and verification module 224 coordinate with a security database 230 to authenticate the user and the developer, and to ensure that the user's data is only being used in the manner the user authorized.

During setup, the user may be directed to EHR server 106, and token module 220 may transmit a login page to the user. The user submits its login credentials (e.g., username and password), and token module 220 checks to see if the login credentials correspond to a registered user in security database 230. If the login information is determined to correspond to a patient enrolled in the EHR system, token module 220 may generate a persistent security token for the patient. The persistent security token may include a globally unique ID (GUID) identifying the patient. Token module 220 may transmit the persistent security token back to the mobile device 104 and data collection application 210, which stores the token with tokens 216. In addition, token module 220 may create an identity profile in security database 230 that verification module 224 can use to authenticate the security token.

In addition to generating a security token for the patient, token module 220 may also generate a security token for the developer. As mentioned above, token module 220 may generate the developer's security token after the developer or developer's application has gone through a certification process with the EHR provider.

After the login process, authorization module 222 may present the patient with additional screens that prompt the patient to authorize data collection application 210 to use one or more APIs. Some APIs may enable data collection application 210 to retrieve background biographical information about the patient. Other APIs may enable data collection application 210 to submit observational data to files only accessible by the patient. Still other APIs may enable data collection application 210 to submit observational data to files accessible by a physician. As described in more detail below, authorization module 222 may prompt and ask the patient whether each of these different types of APIs are authorized.

Once the patient has authorized the API calls and data collection application 210 has received the patient's persistent security token, data collection application 210 can start making API calls. In one embodiment, in addition to receiving the patient security tokens, data collection application 210 receives a list specifying which APIs the patient has authorized.

To service API requests, EHR server 106 uses its verification module 224. Every API call may include the persistent security tokens for the patient and developer, and may specify which API function it seeks to invoke. In response to receipt of the API call, verification module 224 verifies authenticity of the persistent security token for the patient and the persistent security token for the developer of the patient collection device against corresponding data in security database 230. Verification module 224 also may evaluate a record in security database 230 to determine whether the patient has authorized data collection application 210 to make the API call.

As mentioned above, some API calls involve submitting observational data to medical records database 132. To service those APIs calls, a patient data collection module 226 stores the observational data to the patient's file in medical records database 132.

Once recorded in the medical records database 132, the patient may be able to review the observational database through an interface provided by EHR server 106. For example, the data may appear in a timeline of events relating to the patient's health. The timeline may, for example, present the patient's disparate medical events in reverse chronological order. In one embodiment, the observational data may only appear in a view accessible to the patient that lists the patient's disparate medical events in reverse chronological order. Or, if the patient has authorized physician access, the observational data may also appear in views accessible by authorized physicians or members of their practice.

In addition to being useful for tracking purposes, the submitted observational data may also be used to actively provide patient care. In particular, alert module 228 may have rules associated with the observational data. The rules may be set by the patient or an authorized physician's practice. The rules may specify that when the data is outside of a normal range, perhaps specified by the physician, certain actions occur. The action may involve alerting the physician, alerting the patient, or alerting emergency services of the abnormality. In one embodiment, prior to alert module 228 alerting a physician, verification module 224 may determine whether the patient has authorized the physician to be alerted. The alert may involve an e-mail or text including a link to a secure message portal provided by EHR server 106. In addition, the alert may involve sending a fax or an automated phone message. The alert may include a recommended action. For example, if alert module 228 detects a blood sugar level outside of a diabetic patient's normal range, alert module 228 may advise the patient to take an insulin shot. In this way, embodiments can actively provide patient care instead of passively waiting for a patient to report illness or for a physician to personally review results.

The rules configured in alert module 228 may specify how the type of alert may vary depending on the seriousness of the condition or how far the observational data is out of its normal range. For example, if alert module 228 detects a blood sugar level a small amount outside of a diabetic patient's normal range, alert module 228 may remind the patient to take an insulin shot. But, if alert module 228 detects that the blood sugar level is a large amount outside of a diabetic patient's normal range, alert module 228 may contact the physician or emergency services.

Finally, the rules configured in alert module 228 may look at multiple data points over time. For example, if alert module 228 detects that the patient's blood sugar level strays outside of his normal range at a specified frequency, alert module 228 may inform the patient or physician that additional training or education may be necessary. In this way, quality of care may be improved in a seamless, proactive manner.

FIGS. 3A-D are flowcharts illustrating example methods to integrate a patient data collection device and an EHR server. These example methods may be used in operation of the system of FIG. 2.

FIG. 3A illustrates a method 300. Method 300 starts at step 302 by receiving a new order from a physician for a patient to use a data collection application. A doctor, for example during a patient encounter, may prescribe or recommend a data collection application. Similar to how a doctor may order a patient to take a medication, the doctor may order the patient to download an application or purchase a device. In one example, a doctor may diagnose a patient with diabetes. In that example, the EHR server stores a specific record in the medical records database that states that the patient has been diagnosed with diabetes. In addition, the EHR server may store a record indicating that the patient has been prescribed insulin, which is available from a pharmacy. That record for insulin serves as an e-prescription. In addition, the EHR server may store a record indicating that the patient should download an application, purchase a device, or both.

At step 304, EHR server 106 sends a reminder to the patient to purchase the data collection application. To protect the patient's privacy, the reminder may be an email that indicates that the patient has a new message on their EHR portal. The email may include a link that, when selected, redirects the patient to the new message in the EHR portal. Prior to viewing the message, EHR server 106 may verify the authenticity of a security token or require the patient to enter login credentials. The message may remind the patient of the need to purchase the application or device and may provide information on how to make the purchase, including links or buttons to recommended vendors.

When a patient clicks on the link or button, the patient may be redirected to another server, such as, for example, third party developer server 108 or an application marketplace server such as the AppStore available from Apple, Inc. At step 306, the patient downloads the application—such as data collection application 210 in FIG. 2—to the patient's mobile device or purchases the device. The external application is developed by a third party different from the EHR provider. The EHR provider may have worked with the third party developer to embed, for example, a button or link in their application to log in with an EHR server account or to create an EHR server account. Medical data collection application 210 provides that button or link to the user at step 308.

At step 310, medical data collection application 210 receives a user selection of the button and redirects the patient to a login page for EHR server 106. To encourage the patient to trust the login page, the login page may include the logo of the EHR provider. The logo may instill trust because the patient has interacted with their personal health record in the past. The patient can login with their unique EHR server credentials. These transactions, like all other network communications disclosed herein, may be done using Hypertext Transfer Protocol Secure (HTTPS) and secure socket layer (SSL) certificates. The pages may be Hypertext Markup Language (HTML) pages and data may be transmitted in a structure format, such as extendable markup language (XML). The user enters their PHR login credentials, and EHR server 106 receives the credentials at step 312.

After receiving and verifying the patient's credentials, EHR server 106 generates a token for the patient at step 314. Then, at step 316, EHR server 106 prompts the patient with a message that asks whether the patient authorizes this application or application developer to access the patient's biographical information. After receiving this information, the process proceeds to method 330 in FIG. 3B to complete the setup procedure.

Method 330 begins at step 332 when EHR server 106 prompts the patient for authorization to send the observational data to EHR server 106. At step 334, EHR server 106 prompts the patient for authorization to send the observational data to the physician's medical records. Alternatively, steps 332 and 334 may be done as a single prompt.

At step 336, EHR server 106 transmits the data collected from the user to third party developer server 108. In particular, EHR server 106 transmits the persistent security token and an identification of which APIs the patient authorized to third party developer server 108. At step 338, third party developer server 108 stores the data. With that information, third party developer server 108 can make API calls to customize the application according to the patient as illustrated in FIG. 3C.

Figure 3B:
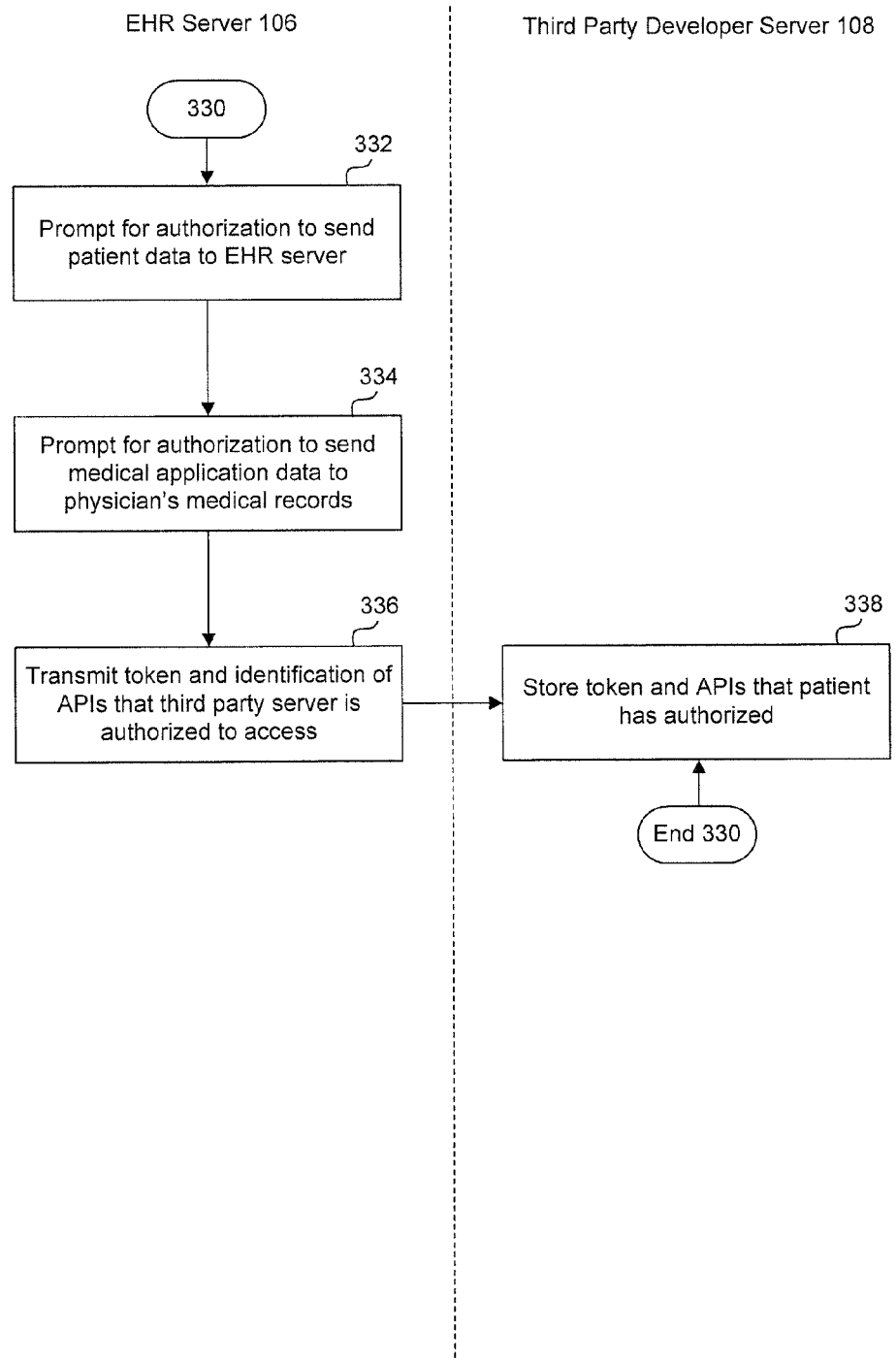
Figure 3C:
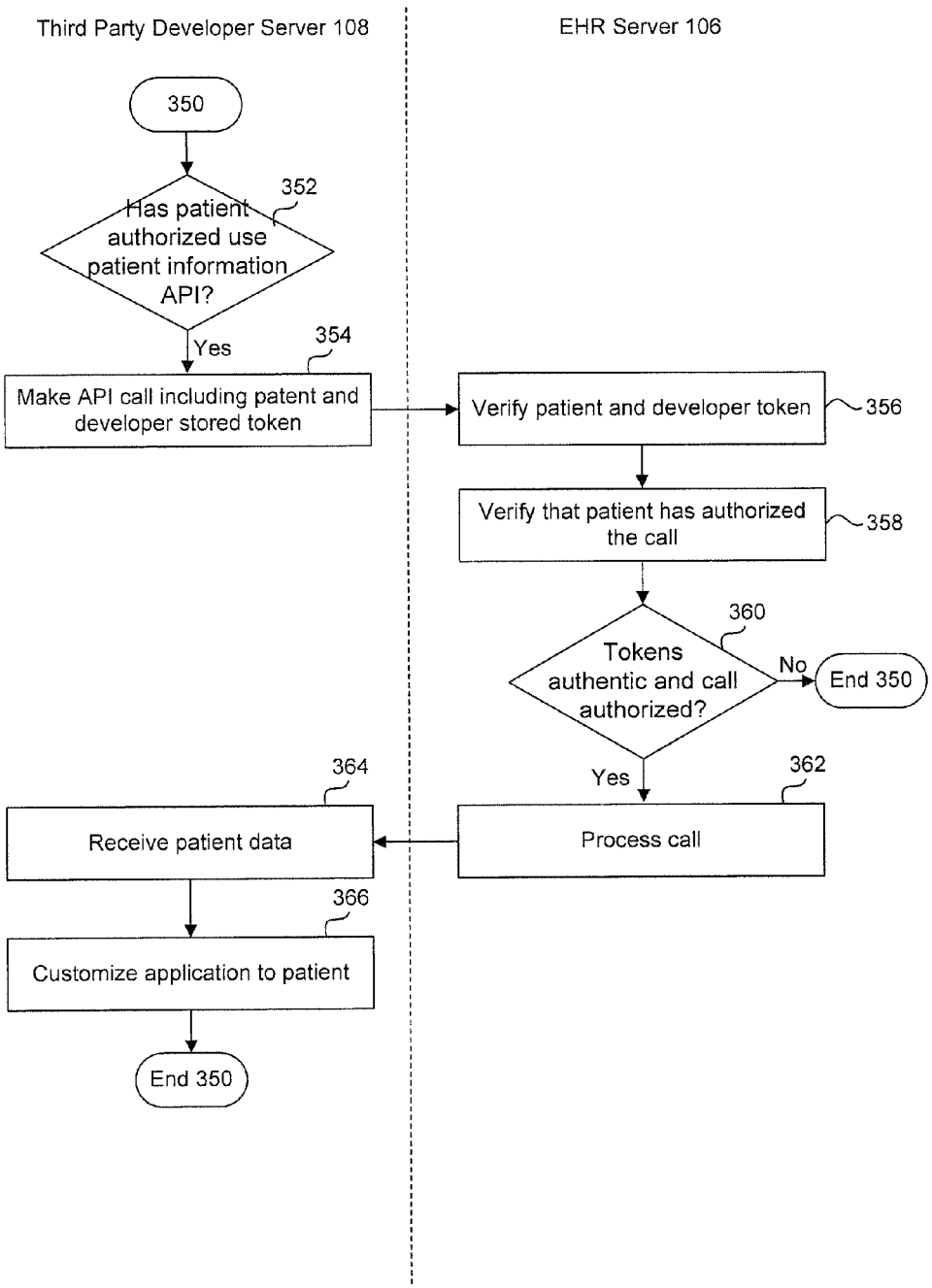

FIG. 3C includes a method 350 that begins by determining whether the patient has authorized use of the patient information API at step 352. This may involve evaluating the information received from EHR server 106 that indicates which APIs the user authorized.

If the patient has not authorized use of the patient biographical information API, third-party developer server 108 makes an API call using the patient and developer tokens. EHR server 106 receives the API call and verifies the authenticity of the patient and developer tokens at step 356. Then, EHR server 106 verifies that the patient authorized the call at step 358. If EHR server 106 determines the tokens to be authentic and the call to be authorized at decision block 360, the call is processed at step 362.

To process the call at step 362, EHR server 106 may retrieve patient biographical information such as the patient's full name, date of birth, gender, geographic location, and other biographical information. EHR server 106 may send the patient data back to third party developer server 108. At step 364, third-party developer server 108 receives the patient data. At step 366, third-party developer server 108 customizes the application to the patient according to the biographical information. The customization may involve, for example, pre-populating fields using the patient biographical information. The customization may also involve, for example, determining whether certain fields are applicable based on the biographical information, and only displaying fields that third party developer server 108 determines to be applicable. While these functions are described as being done by third-party developer 108, a skilled artisan would also recognize that they can also be done by data collection application 210 running on the patient's mobile device.

Figure 3D:
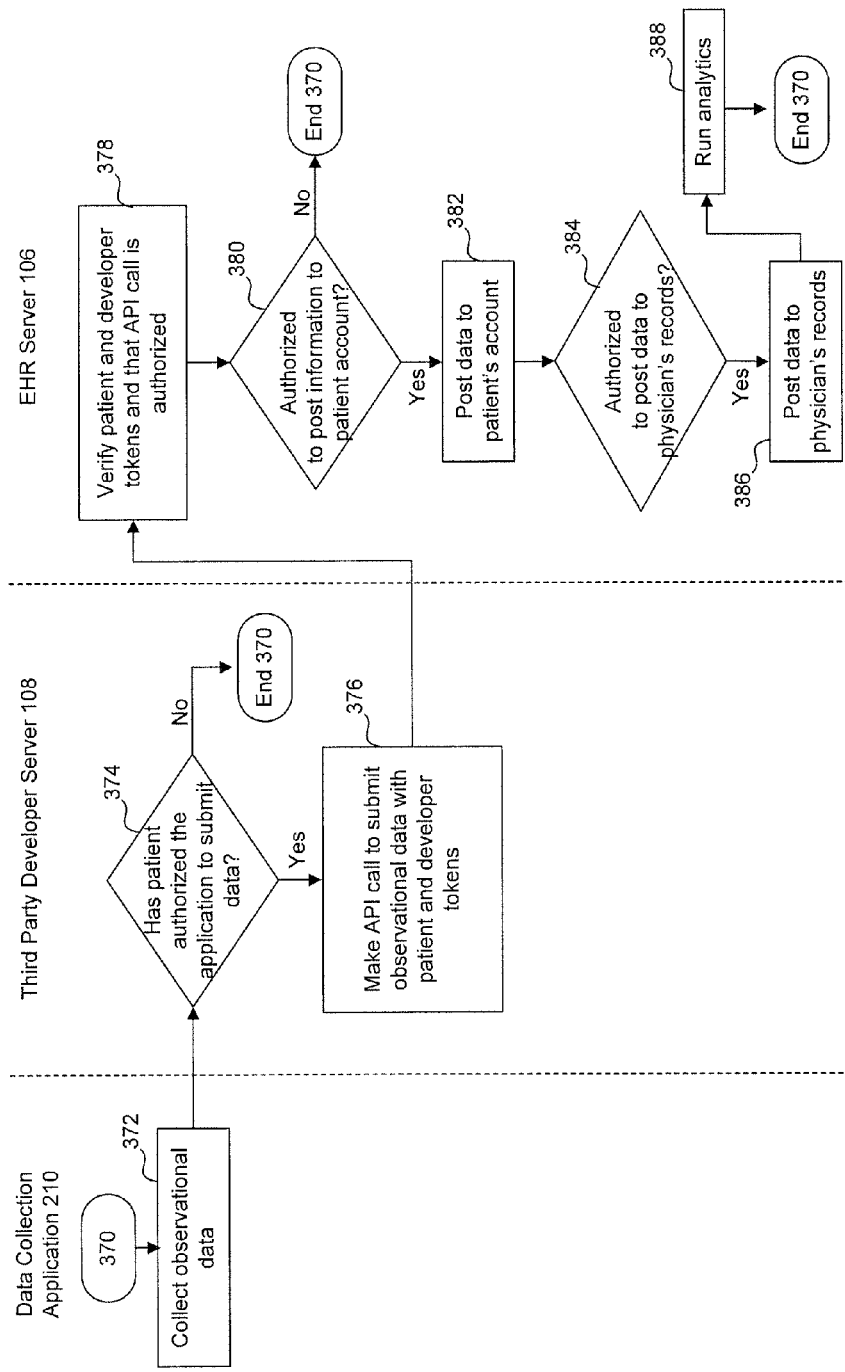

In addition to making API calls for the patient biographical information, data collection application 210 or third-party developer server 108 may also collect observational data about the patient and submit the observational data to the patient's medical records as illustrated in FIG. 3D.

FIG. 3D illustrates a method 370 for submitting observational data to the medical records database. Method 370 begins with data collection application 210 collecting observational data at step 372. To collect the observational data, data collection application 210 may, for example, prompt the user for the relevant information. Alternatively, data collection application 210 may communicate with another device, which senses the data. The observational data may include, for example, vital signs data, such as blood glucose information, heart rate information from, for example, a pacemaker, or blood pressure information. The observational data may describe anything that is collected about the patient during the day, e.g. blood glucose value before a meal, total number of calories output, total number of calories taken in, and weight at a certain point of the day.

Data collection application 210 may submit the information directly to EHR server 106 or, as illustrated in method 370, transmit third-party developer server 108, which in turn transmits the data to EHR server 106.

At decision block 374, third-party developer server 108 determines, based on information received from EHR server 106, whether the patient has authorized the application to submit data to the medical records database. If the patient has authorized the application to submit data, third-party developer server 108 makes an API call to submit the observational data with the patient developer tokens at step 376. The API calls are transmitted to EHR server 106.

At step 378, EHR server 106 verifies the patient and developer tokens and that the API call is authorized. EHR server 106 determines whether the patient has authorized the application to post information to the patient account at decision block 380. If authorized, EHR server 106 posts data to the patient account at step 382. At decision block 384, EHR server 106 determines whether the patient has authorized the application to post information to the physician's records. If authorized, EHR server 106 posts data to the physician's records at step 386.

At step 388, analytics are run against the collected observational data. The observational data may be evaluated against an evidence-based standard deviation based on medical standards or a range set in the doctor's preferences. In addition, analytics may be run to determine whether there is a sudden change in the observational data. For example, EHR server 106 may generate alert if the observed glucose level is 5% or 10% higher than it was at a previous time, such as 15 minutes prior. If it's 5% higher, EHR server 106 may send a message to the patient through his or her EHR portal. And if it's 10% higher, EHR server 106 may send the patient a text message, call the patient's phone, or even dispatch care professionals to check up on the patient.

In this way, by integrating patient data collection applications into electronic medical records, embodiments can track a patient's holistic health information and provide proactive medical care.

Integration of Physician Productivity Device and EHR Server

Figure 4:
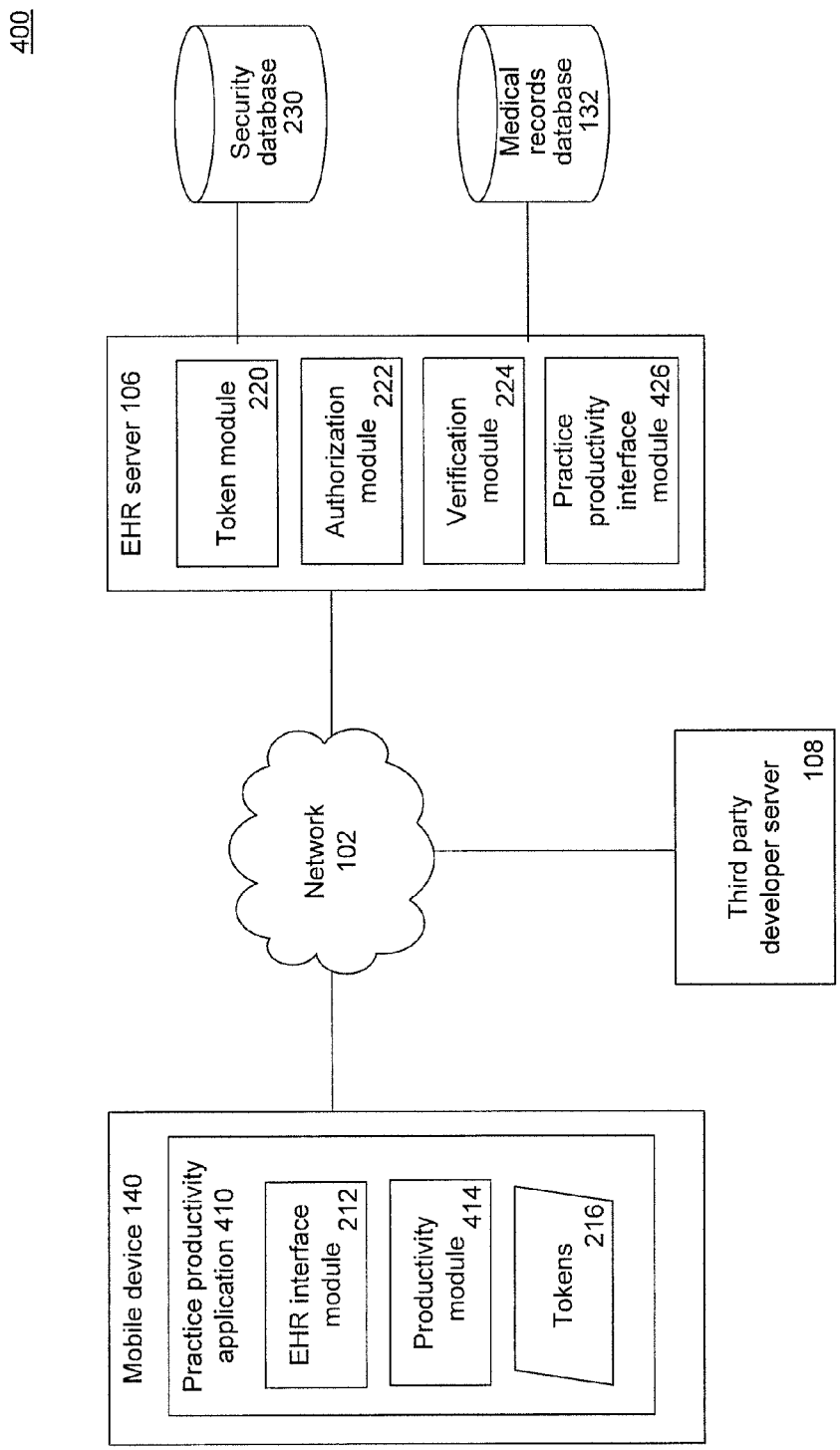
FIG. 4 is a diagram illustrating the physician productivity device and the EHR server of FIG. 1 in greater detail.

Not only can embodiments integrate patient data collection devices with an EHR server as illustrated in FIG. 2, embodiments can also integrate physician productivity devices with the EHR server as illustrated in FIG. 4. FIG. 4 is a diagram illustrating a system 400 that integrates a physician productivity device and an EHR server. While this disclosure sometimes refers to physicians for illustrative purposes, a skilled artisan would recognize that it could be applied to other medical professionals, including nurses and front office staff.

Like system 200 illustrated in FIG. 2, system 400 includes mobile device 140, third-party developer server 108, and EHR server 106 connected via network 102. And, like system 200 illustrated in FIG. 2, EHR server 106 includes a token module 220, an authorization module 222, and a verification module 224, and is coupled to security database 230 and medical records database 132.

In addition, EHR server 106 includes a practice productivity interface module 426, and mobile device 140 includes a practice productivity application 410. Like data collection application 210 in FIG. 2, practice productivity application 410 includes an EHR interface module 212 and tokens 216. In addition, practice productivity application 410 includes a productivity module 414.

Similar to data collection application 210 in FIG. 2, practice productivity application 410 may, for example, be purchased or retrieved from an online application marketplace and installed on mobile device 140. Practice productivity application 410 provides functionality that enables a physician, or the physician's practice, to increase productivity. For example, practice productivity application 410 may be an application that enables a physician to dictate his notes. In other examples, practice productivity application 410 may communicate directly with other devices, such as a scale or blood pressure sensor, to collect data about a patient.

As discussed above, EHR interface module 212 communicates with EHR server 106, either directly or through third-party developer server 108. When operating in practice productivity application 410, EHR interface module 212 may make three different types of API calls: (1) API calls to retrieve patient data from a medical records database on the EHR system; (2) API calls to retrieve practice information from a medical records database on the EHR system; and (3) API calls to submit productivity data. In all three cases, the API calls may include security tokens from tokens 216 that authenticate the physician and developer of the practice productivity application 410.

Productivity module 414 provides functionality productivity for the physician of the physician's practice. As set forth below above, this functionality may include, for example, transcription of doctors' notes or interaction with devices that collect data about a patient.

Like in FIG. 2's system 200, in system 400 token module 220 enables a physician and members of the physician's practice to log in. It receives physician login information that a physician entered on a login portal. In response to receipt of the physician login information, token module 220 determines whether the physician login information corresponds to a physician enrolled in the EHR system. And, if the physician login information is determined to correspond to a physician enrolled in the EHR system, token module 220 generates the persistent security token for the physician and transmits the persistent security token to the practice productivity application.

Not only can token module 220 create tokens, it can also revoke them. The token may need to be revoked, for example, for non-payment of fees, for failing to comply with the terms of use, or in the event of a security breach.

Again like in FIG. 2's system 200, in system 400 authorization module 222 prompts a user, in this case a physician, to authorize the application to execute certain API calls. For example, authorization module 222 may prompt the physician to authorize the practice productivity application to: (i) retrieve practice information, (ii) retrieve patient data, and (iii) submit data to the physician's medical records on the EHR system.

Again like in FIG. 2's system 200, in system 400 verification module 224 determines whether an API call is authenticated and authorized. In response to receipt of the API call, verification module 224 verifies the authenticity of the persistent security token for the physician and the persistent security token for the practice productivity application, and determines whether the physician has authorized the practice productivity application to make the API call.

Practice productivity interface module 426 executes the functionality specified by the API call. As mentioned above, this may involve retrieving information (such as practice information and patient data) from medical records database 132 or submitting productivity information (such as transcribed notes) to medical records database 132.

In one embodiment, medical records database 132 includes a schedule of appointments for the physician, and physician productivity interface module 142 can use the schedule to refine its API functionality. For example, in response to an API call to retrieve patient data, practice productivity interface module 426 may identify which patient is currently scheduled on the physician's schedule of appointments and may send data about the identified patient. In another example, in response to an API call to submit productivity data, practice productivity interface module 426 may identify which patient is currently scheduled on the physician's schedule of appointments and may store the submitted productivity data to the physician's file about the identified patient. The productivity data may be data that help the practice and medical professional be more productive.

FIGS. 5A-E are flowcharts illustrating example methods to integrate the patient data collection device and the EHR server. These methods may be used in operation of system 400 in FIG. 4. FIG. 5 illustrates a method 500 for setting up a new productivity application. Many of the steps described here are similar to steps described above for integration of the data collection application. A skilled artisan would recognize that features of those steps described above can be incorporated into the method here.

Method 500 begins at step 502 by providing a marketplace for practice productivity applications. This may be done, for example, by EHR server 106. For example, EHR server 106 may provide co-marketing that directs doctors to productivity applications that may be useful. EHR server 106 may send e-mails to physicians advertising apps that may be useful to them. The advertising may be selected based on the practice's specialty, size, or other practice information.

At step 504, the physician downloads the application from third-party developer server 108 to the physician's mobile device. Third-party developer server 108 or EHR server 106 may, for example, email the doctor with explicit instructions on what they should do when they download productivity application 410 and install it on the phone.

Because EHR server 106 referred the doctor to third-party developer server 108 to purchase productivity application 410, productivity application 410 may know that the physician uses EHR server 106. Because productivity application 410 knows that the physician uses EHR server 106, the first thing productivity application 410 may present when initiated is EHR server 106's login page at step 506. Alternatively, productivity application 410 may ask the physician to identify the EHR provider used.

At step 508, EHR server 106 receives the physician's EHR credentials, for example the physician's email address and password. In addition to granting access to the EHR server 106's API, the EHR credentials may be used to log the user in to productivity application 410. In this way, productivity application 410 can reuse the EHR credentials that the physician may already use frequently, perhaps daily, to access its patient medical records.

If EHR server 106 determines that EHR credentials are correct, it prompts the doctors for authorization of different APIs at steps 510, 512, and 514. At step 510, EHR server 106 prompts the physician to determine whether she authorizes productivity application 410 to post information to the physician's medical records.

At step 512, EHR server 106 prompts the physician to determine whether she authorizes productivity application 410 to access the physician's patient records. EHR server 106 may have several different ways to query the patient records, including retrieving a list of all the patients, retrieving detailed records for a specific patient, or retrieving records for the patient that the doctor is currently scheduled to see. The doctor may authorize all of these different API calls or may authorize the API calls at a more granular level.

At step 514, EHR server 106 prompts the physician to determine whether she authorizes productivity application 410 to access to the physician's practice information. The practice information may include the other users in the practice, the staff, the nurses, and the front office people. Providing this information to productivity application 410 may, for example, improve its experience because it would enable the doctor to quickly select a nurse that helped check in a patient. The practice information may also include a specialty, the state that the practice is operating in, where the physician is licensed to practice, and insurance that the physician accepts.

Figure 5A:
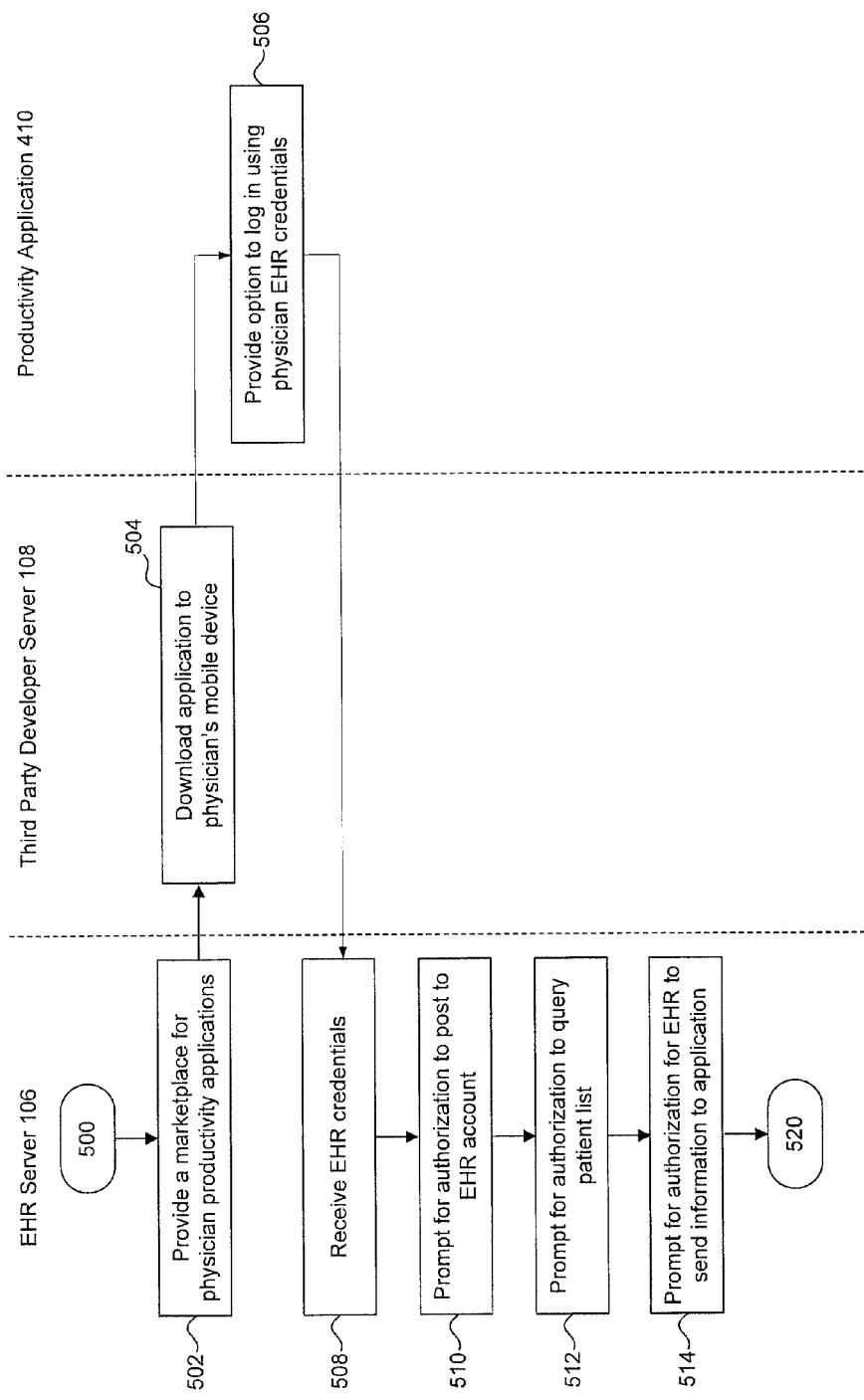
FIGS. 5A-E are flowcharts illustrating example methods to integrate the patient data collection device and the EHR server.
Figure 5B:
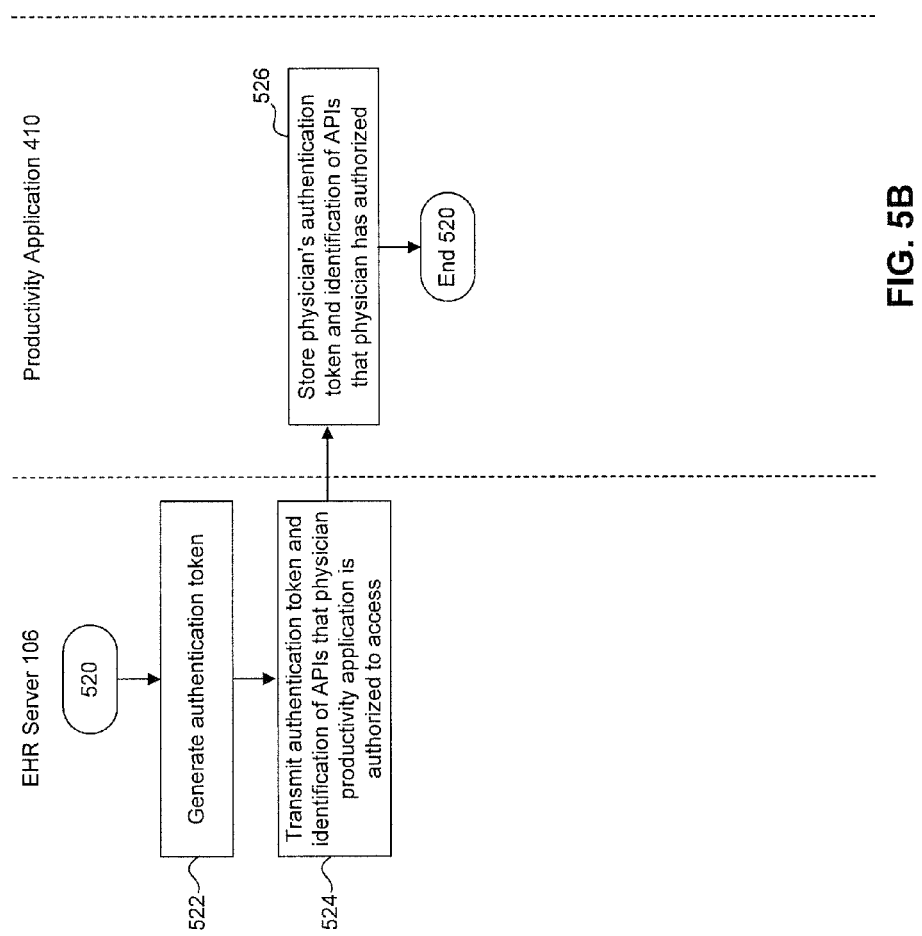

After completing these prompts, the process goes to method 520 in FIG. 5B to complete setup of productivity application 410.

Method 520 begins with the step 522 when EHR server 106 generates the authentication token. At step 524, EHR server 106 transmits the authentication token generated in step 522 and identification of the APIs that the doctors authorized. At step 526, EHR server 106 stores the authentication token and identification of the APIs that the doctors authorized.

Figure 5C:
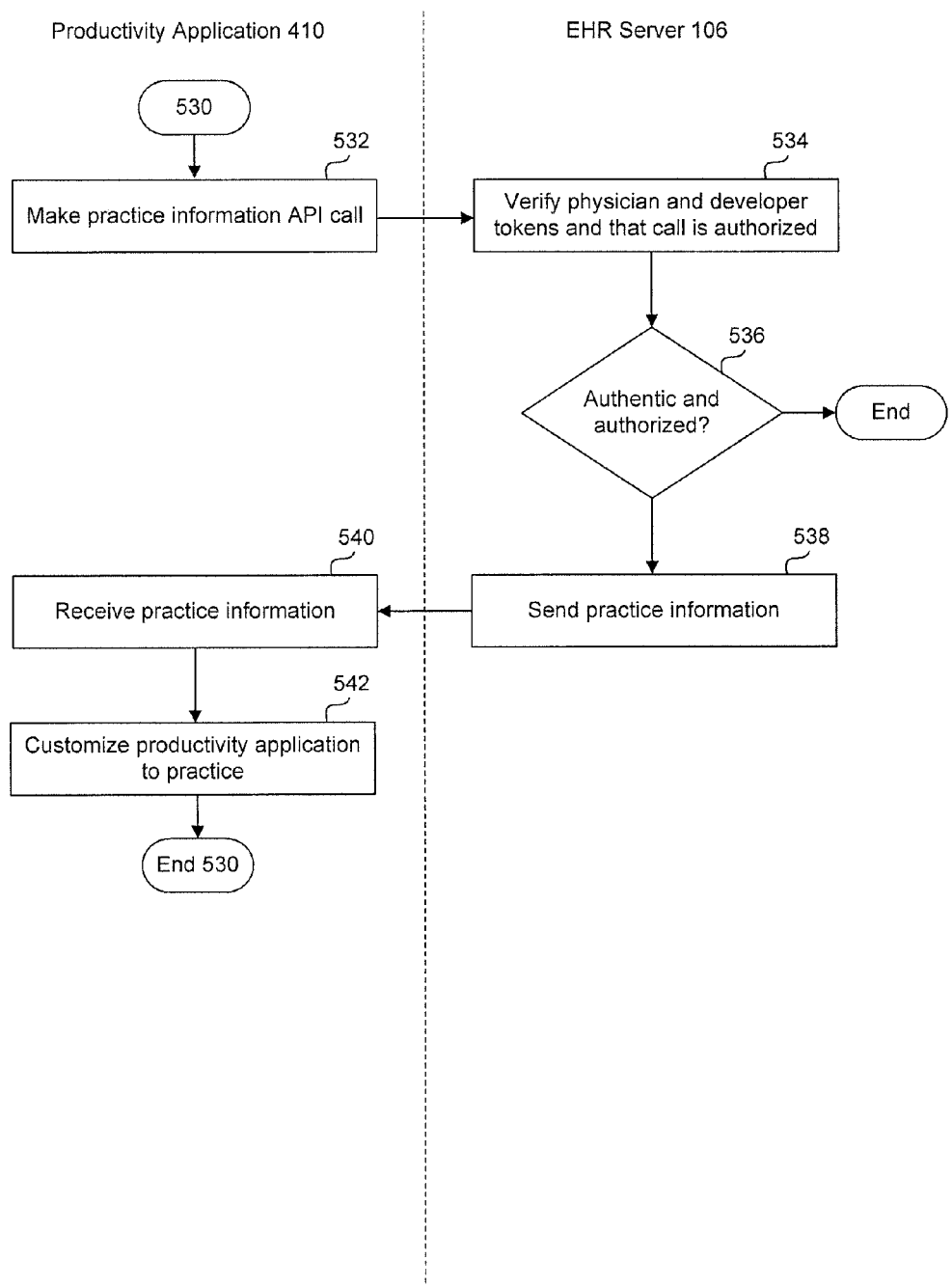
Figure 5D:
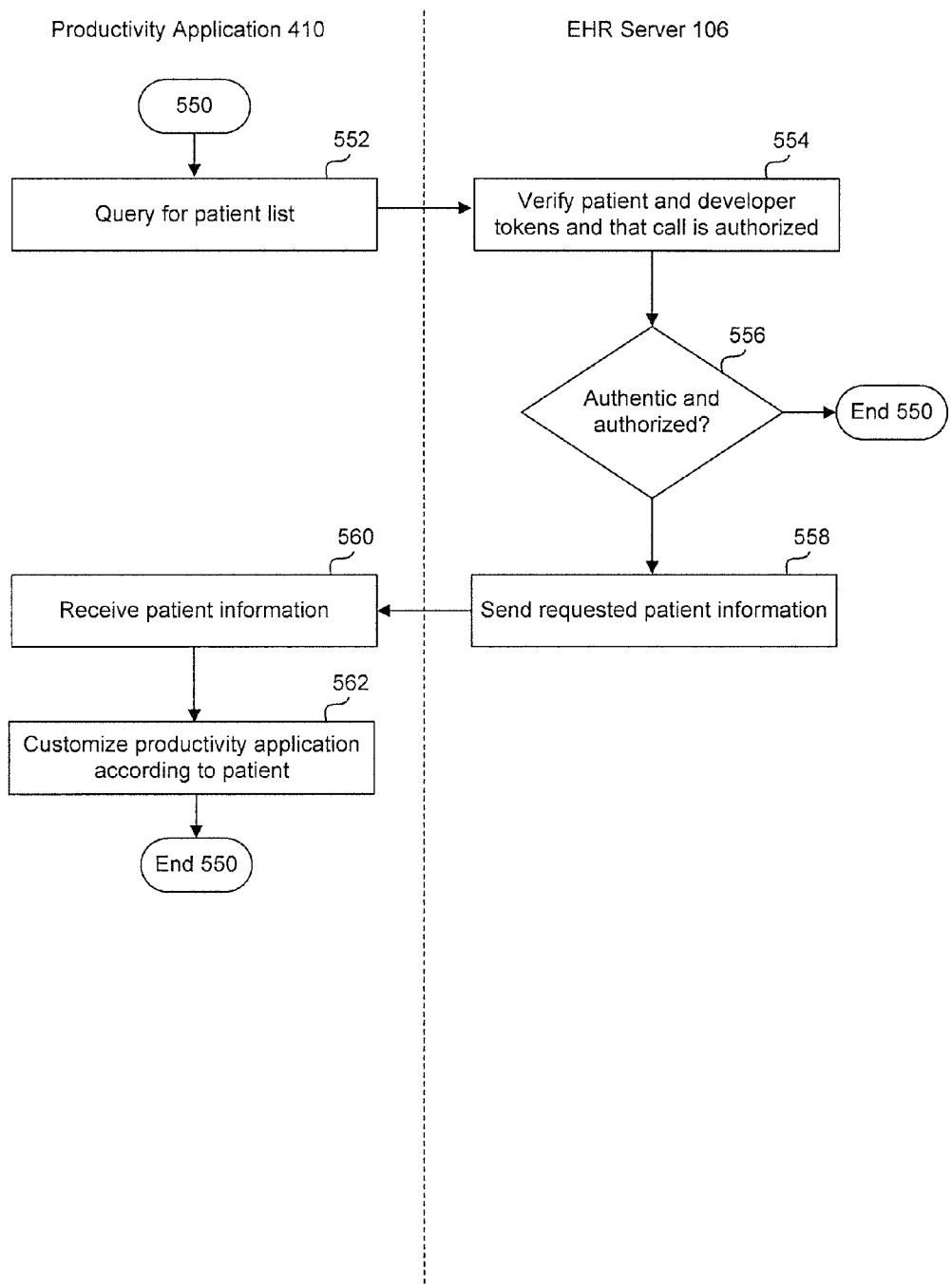
Figure 5E:
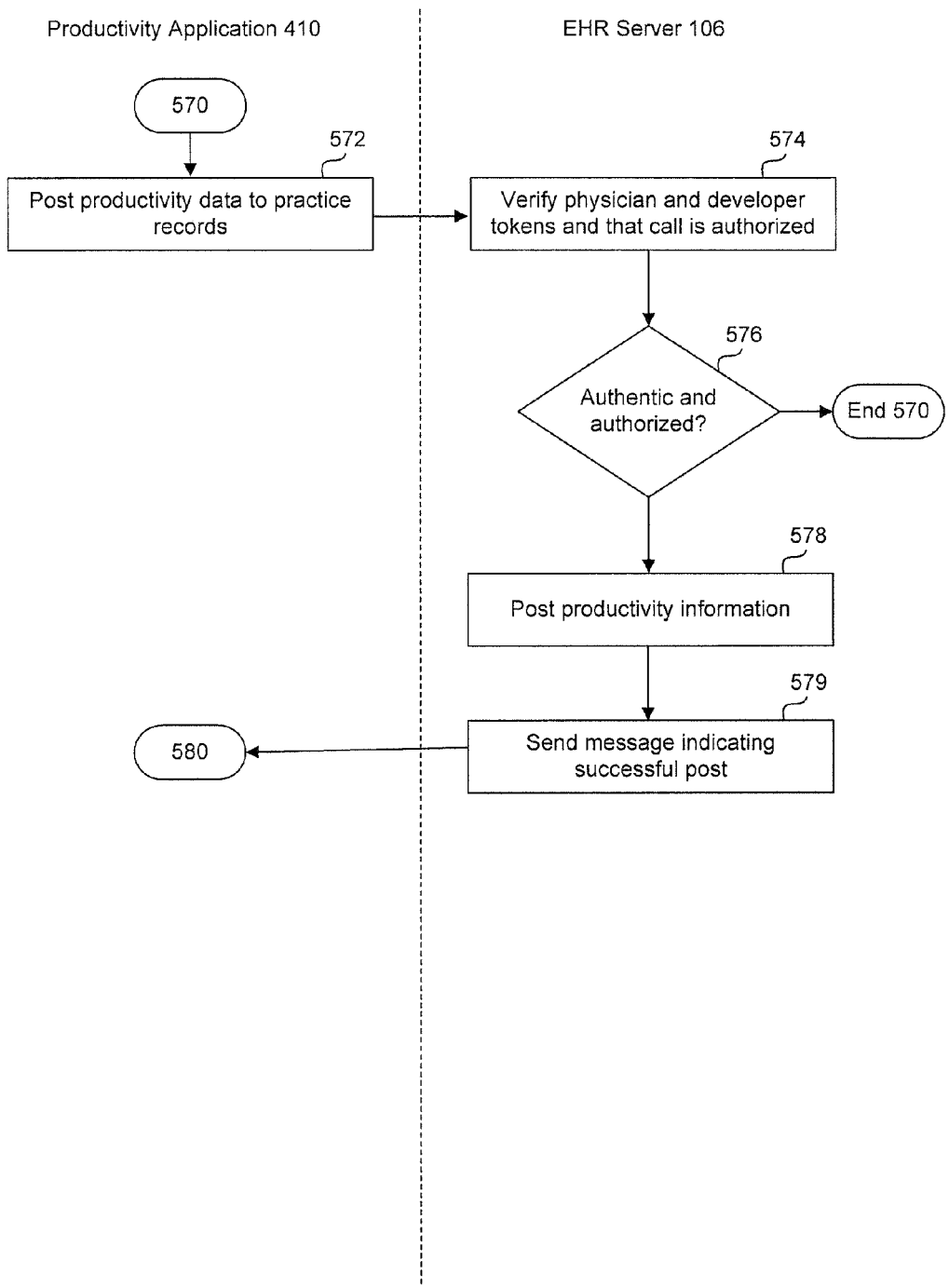

With that information, productivity application 410 can make API calls as illustrated in FIGS. 5C-E. Though not shown in FIGS. 5C-E, productivity application 410 can also check to see if a call is authorized prior to making it.

FIG. 5C illustrates a method 530 for retrieving practice information. Method 530 begins when productivity application 410 makes an API call to retrieve practice information at step 532. The API call includes tokens for the physician and productivity application 410's developer. The API call is sent to EHR server 106, which verifies the physician and developer tokens, and that the physician has authorized the call to be made at step 534. If EHR server 106 determines that the call is authorized and authentic at decision block 536, EHR server 106 sends the practice information to productivity application 410 at step 538. Productivity application 410 receives the practice information at step 540. Then, based on the practice information, productivity application 410 customizes the interfaces and functionality provided to the physician at step 542.

FIG. 5D illustrates a method 550 for retrieving practice information. Method 550 begins when productivity application 410 makes an API call to retrieve patient information at step 552. The API call includes tokens for the physician and productivity application 410's developer. The API call is sent to EHR server 106, which verifies the physician and developer tokens, and that the physician has authorized the call to be made at step 554. If EHR server 106 determines that the call is authorized and authentic at decision block 556, EHR server 106 sends the patient information to productivity application 410 at step 558. Productivity application 410 receives the patient information at step 560. Then, based on the practice information, productivity application 410 customizes the interfaces and functionality provided to the physician at step 562.

FIG. 5E illustrates a method 570 for submitting information to the EHR Server. Method 570 begins when productivity application 410 makes an API call to retrieve patient information at step 572. The API call includes tokens for the physician and productivity application 410's developer. The API call is sent to EHR server 106, which verifies the physician and developer tokens, and that the physician has authorized the call to be made at step 574. If EHR server 106 determines that the call is authorized and authentic at decision block 576, EHR server 106 stores the productivity information at step 578. Finally, at step 579, a message is sent back to productivity application 410 indicating that the data was successfully posted.

The API call can include an identifier for a specific patient. In that case, EHR server 106 may associate the stored productivity information with a patient record. Alternatively, the API call can include a patient name but not an identifier specific for that patient. In that case, but EHR server 106 may store the productivity information in a temporary file location. Then, the physician or member of the physician's practice may periodically evaluate the data in the temporary file location to associate the data with one or more specific medical records.

In this way, embodiments can integrate a practice productivity application with an EHR server.

Example Computing Devices

Each of the servers and modules in FIGS. 1, 2, and 4 may be implemented on the same or different computing devices in hardware, software, or any combination thereof. Such computing devices can include, but are not limited to, a personal computer, a mobile device such as a mobile phone, workstation, embedded system, game console, television, set-top box, or any other computing device. Further, a computing device can include, but is not limited to, a device having a processor and memory, including nontransitory memory, for executing and storing instructions. The memory may tangibly embody the data and program instructions. Software may include one or more applications and an operating system. Hardware can include, but is not limited to, a processor, memory, and graphical user interface display. The computing device may also have multiple processors and multiple shared or separate memory components. For example, the computing device may be a part of or the entirety of a clustered computing environment or server farm.

The persistent security tokens disclosed herein may, for example, be Open Authentication or OpenID tokens.

Figure 6:
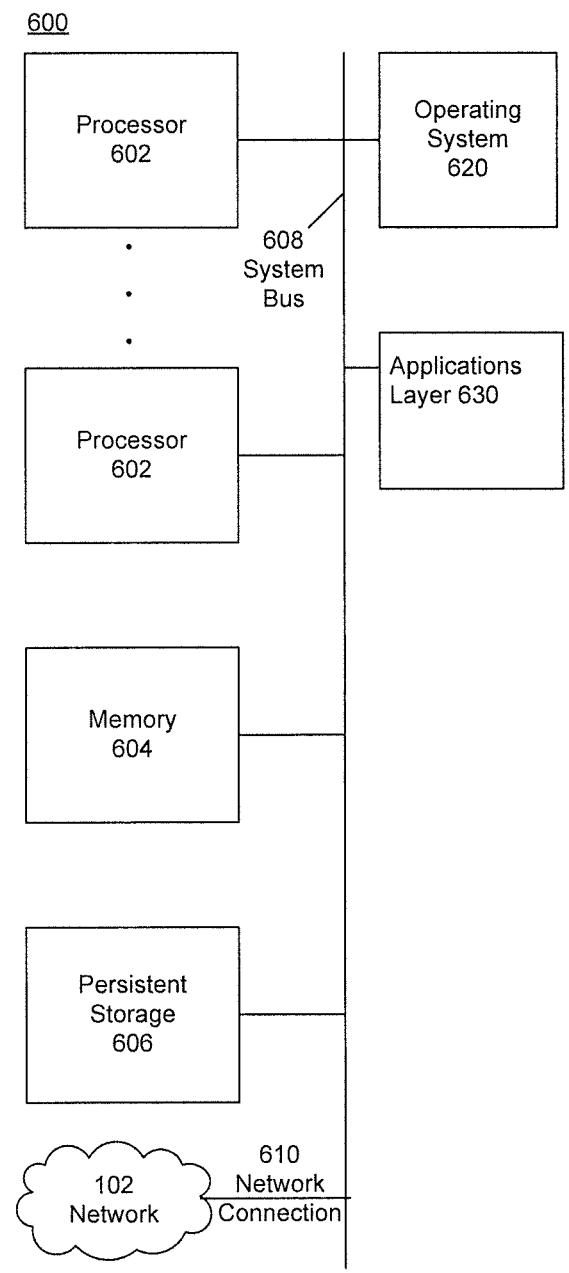
FIG. 6 is a diagram illustrating an example computing device, according to an embodiment.

An example computing device is illustrated in FIG. 6. FIG. 6 is a diagram illustrating a computing device 600 that accesses a network 102 over a network connection 610 that provides computing device 600 with telecommunications capabilities. Computing device 600 uses an operating system 620 as software that manages hardware resources and coordinates the interface between hardware and software.

In an embodiment, computing device 600 contains a combination of hardware, software, and firmware constituent parts that allow it to run an applications layer 630. Computing device 600, in embodiments, may be organized around a system bus 608, but any type of infrastructure that allows the hardware infrastructure elements of computing device 600 to communicate with and interact with each other may also be used.

Processing tasks in the embodiment of FIG. 6 are carried out by one or more processors 602. However, it should be noted that various types of processing technology may be used here, including multi-core processors, multiple processors, or distributed processors. Additional specialized processing resources such as graphics, multimedia, or mathematical processing capabilities may also be used to aid in certain processing tasks. These processing resources may be hardware, software, or an appropriate combination thereof. For example, one or more of processors 602 may be a graphics-processing unit (GPU). In an embodiment, a GPU is a processor that is a specialized electronic circuit designed to rapidly process mathematically intensive applications on electronic devices. The GPU may have a highly parallel structure that is efficient for parallel processing of large blocks of data, such as mathematically intensive data common to computer graphics applications, images and videos.

In order to manipulate data in accordance with embodiments describe herein, processors 602 access a memory 604 via system bus 608. Memory 604 is nontransitory memory, such as random access memory (RAM). Memory 604 may include one or more levels of cache. Memory 604 has stored therein control logic (i.e., computer software) and/or data. For data that needs to be stored more permanently, processors 602 access persistent storage 606 via system bus 608. Persistent storage 606 may include, for example, a hard disk drive and/or a removable storage device or drive. A removable storage drive may be an optical storage device, a compact disc drive, flash memory, a floppy disk drive, a magnetic tape drive, tape backup device, and/or any other storage device/drive.

Processors 602, memory 604, and persistent storage 606 cooperate with operating system 620 to provide basic functionality for computing device 600. Operating system 620 provides support functionality for applications layer 630.

Network connection 610 enables computer device 600 to communicate and interact with any combination of remote devices, remote networks, remote entities, etc. For example, network connection 610 may allow computer device 600 to communicate with remote devices over network 102, which may be a wired and/or wireless network, and which may include any combination of LANs, WANs, the Internet, etc. Control logic and/or data may be transmitted to and from computer device 600 via network connection 610.

Applications layer 630 may house various modules and components. For example, the applications and modules in FIGS. 1, 2, and 4 may be included in applications layer 630.

It should be noted that computer-readable medium embodiments may include any physical medium which is capable of encoding instructions that may subsequently be used by a processor to implement methods described herein. Example physical media may include floppy discs, optical discs (e.g. CDs, mini-CDs, DVDs, HD-DVD, Blu-ray), hard drives, punch cards, tape drives, flash memory, or memory chips. However, any other type of tangible, persistent storage that can serve in the role of providing instructions to a processor may be used to store the instructions in these embodiments.

Comprehensive EHR System

Figure 7:
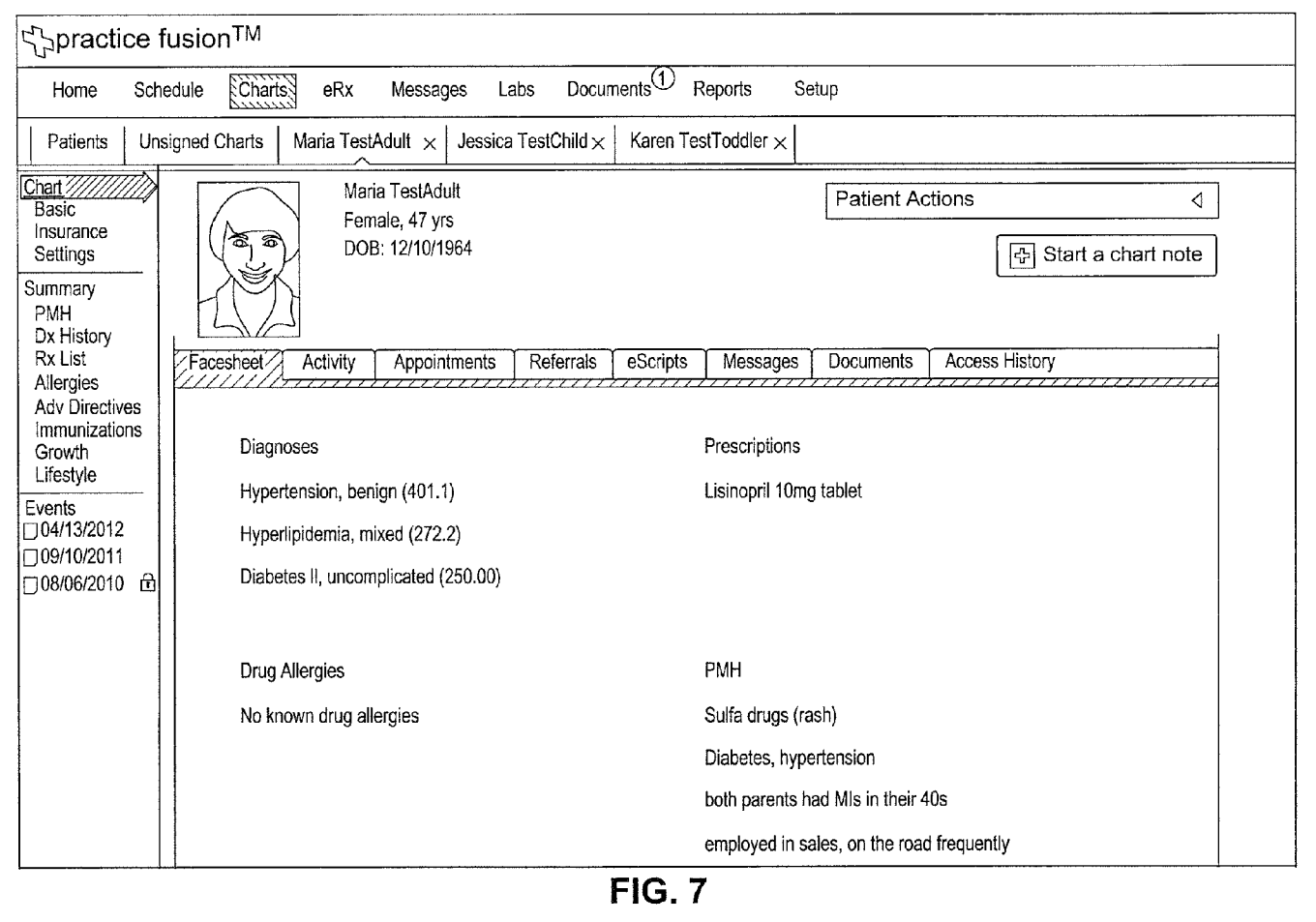

An example of a conventional medical record in an EHR is illustrated in FIG. 7. A comprehensive EHR system includes a variety of components. Components of EHR systems vary from vendor to vendor and from setting to setting. For example, an EHR system in which embodiments of the present invention can be used may also include: (1) an electronic prescription (eRx) component, (2) a clinical and radiology laboratory component, (3) a transfer of care component, (4) a scheduling component, (5) a billing service component, and (6) patient portal component.

The electronic prescription component provides medical professionals capabilities to electronically generate and transmit prescriptions for patients' medications. Some EHR systems enable prescribers to view their patients' prescription benefit information at the point of care and select medications that are on formulary and covered by the patient's drug benefit. This informs physicians of potential lower cost alternatives (such as generic drugs) and reduces administrative burden of pharmacy staff and physicians related to benefit coverage.

The clinical and radiology laboratory component allows medical professionals to integrate with clinical laboratories to electronically receive and incorporate clinical laboratory tests and results into a patient's chart and create computerized provider order entry ("CPOE") clinical laboratory orders. This component can also support functionality that enables medical professionals to electronically receive and incorporate radiology laboratory test results (e.g., x-ray, ultrasound, MRI, PET/CT scan, mammography) into a patient's chart.

Medical professionals can use the transfer of care component to transmit referrals electronically to other EHR users or to non-users by facsimile. Additionally, some EHR systems support electronically creating and transmitting consolidated continuity of care documents.

The scheduling component offers functionality that allows healthcare providers to manage their appointments with an electronic schedule that can be integrated into a practice's workflow.

The billing service component offers medical professionals the ability to electronically generate and transmit superbills. Superbills are the data source for the creation of a healthcare claim. The billing service component can transmit superbills to medical billing software accounts controlled by the professionals' offices or their billing service providers. This component also allows a healthcare professional to save a superbill and transmit it to the health care professional's billing account with the billing software vendor.

The patient portal component allows medical professionals to grant their patients an online means to view, download, and transmit their health information, often called the personal health record (PHR). This component also provides patients with the ability to review their physicians and send and receive secure messages directly to and from their physicians.

Together, these components leverage the benefits of EHRs while mitigating the risks.

CONCLUSION

Identifiers, such as "(a)," "(b)," "(i)," "(ii)," etc., are sometimes used for different elements or steps. These identifiers are used for clarity and do not necessarily designate an order for the elements or steps.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A computer-implemented method for integrating a practice productivity application into an electronic health records (EHR) system with an EHR server, comprising:
   prompting a medical professional for authorization information indicating whether the medical professional authorizes the practice productivity application to retrieve the medical professional's patient data from the medical records database;
   storing the authorization information at the EHR server;
   receiving, from the practice productivity application, an application programming interface (API) call to retrieve patient data from a medical records database on the EHR system, the API call including a persistent security token for the medical professional and a persistent security token for a developer of the practice productivity application;
   in response to receipt of the API call:
   authenticating the persistent security token for the medical professional and the persistent security token for the practice productivity application;
   retrieving the stored authorization information at the EHR server;
   determining, at the EHR server, whether the retrieved authorization information stored on the EHR server indicates that the medical professional has authorized the practice productivity application to retrieve the medical professional's patient data from the medical records database; and
   based on the authenticating step, indicating that the medical professional's and developer's security tokens are determined to be authentic and the authorization information indicating that the authorization information indicates that the practice productivity application is authorized, sending, to the practice productivity application, the patient data such that the practice productivity application provides a user experience customized according to the patient data.

2. The method of claim 1, further comprising:
   receiving medical professional login information that a medical professional entered on a login portal;
   in response to receipt of the medical professional login information:
   determining, at the EHR server, whether the medical professional login information corresponds to a medical professional enrolled in the EHR system;
   when the medical professional login information is determined to correspond to a medical professional enrolled in the EHR system, generating, at the EHR server, the persistent security token for the medical professional; and
   transmitting, over a network from the EHR server, the persistent security token to the practice productivity application.

3. The method of claim 1, further comprising:
   prompting the medical professional to authorize the practice productivity application to: (i) retrieve practice information, and (ii) submit data to the medical professional's medical records on the EHR system.

4. The method of claim 1, wherein the medical records database includes a schedule of appointments for the medical professional, further comprising:
    on the EHR server, retrieving, from the medical records database, patient data for the patient that is currently scheduled on the schedule of appointments, and
    wherein the sending comprising sending the retrieved patient data to the practice productivity application.

5. The method of claim 1, further comprising:
    receiving another API call to retrieve practice information from a medical records database on the EHR system, the other API call including the persistent security token for the medical professional and the persistent security token for the developer of the practice productivity application;
    in response to receipt of the other API call:
    verifying authenticity of the persistent security token for the medical professional and the persistent security token for the developer of the practice productivity application;
    determining whether the medical professional has authorized the practice productivity application to retrieve practice information; and
    when the medical professional's and developer's security tokens are determined to be authentic and the medical professional is determined to have authorized the practice productivity application to retrieve practice information, transmitting, to the practice productivity application, practice information about the practice from the medical records database such that the practice productivity application customizes the medical professional's interface according to the practice information.

6. The method of claim 1, further comprising:
    receiving another API call to submit productivity data to the medical records database on the EHR system, the other API call including the submitted productivity data, the persistent security token for the medical professional and the persistent security token for the developer of the practice productivity application;
    in response to receipt of the other API call:
    verifying authenticity of the persistent security token for the medical professional and the persistent security token for the developer of the practice productivity application;
    determining whether the medical professional has authorized the practice productivity application to submit productivity data; and
    when the medical professional's and developer's security tokens are determined to be authentic and the medical professional is determined to have authorized the practice productivity application to submit productivity data, storing the submitted productivity data to the medical professional's file in the medical records database.

7. The method of claim 6, wherein the medical records database includes a schedule of appointments for the medical professional, further comprising:
    identifying which patient is currently scheduled on the schedule of appointments, and
    wherein the storing (h) comprising storing the submitted productivity data to the medical professional's file about the identified patient.

8. The method of claim 1, wherein the medical professional's and developer's security tokens are each Open Authentication or OpenID tokens.

9. The method of claim 1, further comprising:
    revoking the medical professional's security token.

10. A system for integrating a practice productivity application into an electronic health records (EHR) system, comprising:
    a computing device;
    a medical records database;
    an EHR server, implemented on the computing device, that prompts a medical professional for authorization information indicating whether the medical professional authorizes the practice productivity application to retrieve the medical professional's patient data from the medical records database, stores the authorization information at the EHR server, receives, from the practice productivity application, an application programming interface (API) call to retrieve patient data from the medical records database on the EHR system, the API call including a persistent security token for the medical professional and a persistent security token for a developer of the practice productivity application;
    a verification module, implemented on the computing device, that, in response to receipt of the API call: (i) authenticates the persistent security token for the medical professional and the persistent security token for the practice productivity application, (ii) retrieves the stored authorization information, and (iii) determines whether the medical professional has authorized the practice productivity application to retrieve the medical professional's patient data from the medical records database; and
    a practice productivity interface module that, based on whether the medical professional's and developer's security tokens are determined to be authentic and the retrieved authorization information stored on the EHR server indicates that the practice productivity application is authorized, sends, to the practice productivity application, the patient data such that the practice productivity application provides a user experience customized according to the patient data.

11. The system of claim 10, further comprising:
    a token module that: (i) receives medical professional login information that a medical professional entered on a login portal, (ii) in response to receipt of the medical professional login information, determines, at the EHR server, whether the medical professional login information corresponds to a medical professional enrolled in the EHR system, (iii) when the medical professional login information is determined to correspond to a medical professional enrolled in the EHR system, generating, at the EHR server, the persistent security token for the medical professional, and (iv) again when the medical professional login information is determined to correspond to a medical professional enrolled in the EHR system, transmits the persistent security token to the practice productivity application.

12. The system of claim 10, further comprising:
    an authorization module that prompts the medical professional to authorize the practice productivity application to: (i) retrieve practice information, (ii) retrieve patient data, and (iii) submit data to the medical professional's medical records on the EHR system.

13. The system of claim 10, wherein the medical records database includes a schedule of appointments for the medical professional, and
    wherein the medical professional productivity interface module on the EHR server, retrieves, from the medical records database, patient data for the patient that is currently scheduled on the schedule of appointments and sends the retrieved patient data to the practice productivity application.

14. The system of claim 10, wherein the EHR server receives another API call to retrieve practice information from a medical records database on the EHR system, the other API call including the persistent security token for the medical professional and the persistent security token for the developer of the practice productivity application, wherein the verification module, in response to receipt of the other API call: (i) verifies authenticity of the persistent security token for the medical professional and the persistent security token for the developer of the practice productivity application and (ii) determines whether the medical professional has authorized the practice productivity application to retrieve practice information, and wherein the medical professional productivity interface module, when the medical professional's and developer's security tokens are determined to be authentic and the medical professional is determined to have authorized the practice productivity application to retrieve practice information, transmits, to the practice productivity application, practice information about the practice from the medical records database such that the practice productivity application customizes the medical professional's interface according to the practice information.

15. The system of claim 10, wherein the EHR server receives another API call to submit productivity data to the medical records database on the EHR system, the other API call including the submitted productivity data, the persistent security token for the medical professional and the persistent security token for the developer of the practice productivity application, wherein the verification module, in response to receipt of the other API call: (i) verifies authenticity of the persistent security token for the medical professional and the persistent security token for the developer of the practice productivity application, (ii) determines whether the medical professional has authorized the practice productivity application to submit productivity data, and (iii) when the medical professional's and developer's security tokens are determined to be authentic and the medical professional is determined to have authorized the practice productivity application to submit productivity data, stores the submitted productivity data to the medical professional's file in the medical records database.

16. The system of claim 15, wherein the medical records database includes a schedule of appointments for the medical professional, and wherein the medical professional productivity interface module that: (i) identifies which patient is currently scheduled on the schedule of appointments and (ii) stores the submitted productivity data to the medical professional's file about the identified patient.

17. The system of claim 10, wherein the medical professional's and developer's security tokens are each Open Authentication or OpenID tokens.

18. The system of claim 10, wherein the token module revokes the medical professional's security token.

19. A program storage device tangibly embodying a program of instructions executable by at least one machine to perform a method for integrating a practice productivity application into an electronic health records (EHR) system with an EHR server, said method comprising:

prompting a medical professional for authorization information indicating whether the medical professional authorizes the practice productivity application to retrieve the medical professional's patient data from the medical records database;

storing the authorization information at the EHR server;

receiving, from the practice productivity application, an application programming interface (API) call to retrieve patient data from a medical records database on the EHR system, the API call including a persistent security token for the medical professional and a persistent security token for a developer of the practice productivity application;

in response to receipt of the API call:

authenticating the persistent security token for the medical professional and the persistent security token for the practice productivity application;

retrieving the stored authorization information;

determining whether the retrieved authorization information indicates that the medical professional has authorized the practice productivity application to retrieve the medical professional's patient data from the medical records database; and based on whether the medical professional's and developer's security tokens are determined to be authentic and whether the authorization information indicates that the practice productivity application is authorized, sending, to the practice productivity application, the patient data such that the practice productivity application provides a user experience customized according to the patient data.

20. The program storage device of claim 19, the method further comprising:

receiving another API call to retrieve practice information from a medical records database on the EHR system, the other API call including the persistent security token for the medical professional and the persistent security token for the developer of the practice productivity application;

in response to receipt of the other API call:

verifying authenticity of the persistent security token for the medical professional and the persistent security token for the developer of the practice productivity application;

determining whether the medical professional has authorized the practice productivity application to retrieve practice information; and when the medical professional's and developer's security tokens are determined to be authentic and the medical professional is determined to have authorized the practice productivity application to retrieve practice information, transmitting, to the practice productivity application, practice information about the practice from the medical records database such that the practice productivity application customizes the medical professional's interface according to the practice information.

21. A computer-implemented method for integrating a practice productivity application into an electronic health records (EHR) system, comprising:

prompting for authorization information indicating whether the medical professional authorizes the practice productivity application to retrieve the medical professional's practice information from the medical records database;

storing the authorization information at the EHR server;

receiving, from the practice productivity application, an application programming interface (API) call to retrieve practice information from a medical records database on the EHR system, the API call including a persistent security token for the medical professional and a persistent security token for a developer of the practice productivity application;

in response to receipt of the API call:
authenticating of the persistent security token for the medical professional and the persistent security token for the practice productivity application;
retrieving the stored authorization information;
determining, at the EHR server, whether the retrieved authorization information indicates that the medical professional has authorized the practice productivity application to retrieve the medical professional's practice information from the medical records database; and
based on whether the medical professional's and developer's security tokens are determined to be authentic and whether the authorization information indicates that the practice productivity application is authorized, sending, to the practice productivity application, the practice information such that the practice productivity application provides a user experience customized according to the practice information.

* * * * *